United States Patent [19]
Seidenberg

[11] Patent Number: 5,147,203
[45] Date of Patent: Sep. 15, 1992

[54] AIR/WATER DELIVERY SYSTEM FOR USE WITH DENTAL ILLUMINATION DEVICES

[76] Inventor: Jack W. Seidenberg, 936 Madison St., Woodmere, N.Y. 11598

[21] Appl. No.: 737,774

[22] Filed: Jul. 30, 1991

[51] Int. Cl.$^5$ ............................................. A61C 3/00
[52] U.S. Cl. ....................................... 433/29; 433/82; 433/85
[58] Field of Search ............................ 433/29, 82, 85

[56] References Cited

U.S. PATENT DOCUMENTS

| | | | |
|---|---|---|---|
| 2,012,886 | 8/1935 | Lowry | 433/85 |
| 4,020,556 | 5/1977 | Sotman | 433/29 |
| 4,872,837 | 10/1989 | Issalene et al. | 433/29 |
| 4,902,225 | 2/1990 | Lohn | 433/29 |
| 5,007,837 | 4/1991 | Werly | 433/29 |

FOREIGN PATENT DOCUMENTS 797533 7/1958 United Kingdom ................. 433/82

*Primary Examiner*—John J. Wilson
*Attorney, Agent, or Firm*—Schweitzer Cornman & Gross

[57] ABSTRACT

An apparatus allowing the provision of light and/or water at the tip of a dental illumination light curing device normally provided without such capability includes a pair of supply lines terminating at their remote end in an adapter capable of connection to a standard air/water connection as found on a dental pedestal. The local ends of the supply lines terminate at the neck of the illuminator, where they are supported upon the neck by a clamp, and interconnect with a pair of nozzle tubes. The nozzle tubes have exits at the illuminator tip, and are secured thereto in a removable manner. The modular nature of the apparatus allows removal and exchange of the nozzle elements as desired to accommodate differing illuminator neck shapes and lengths and permit sterilization and replacement of the nozzle elements.

3 Claims, 2 Drawing Sheets

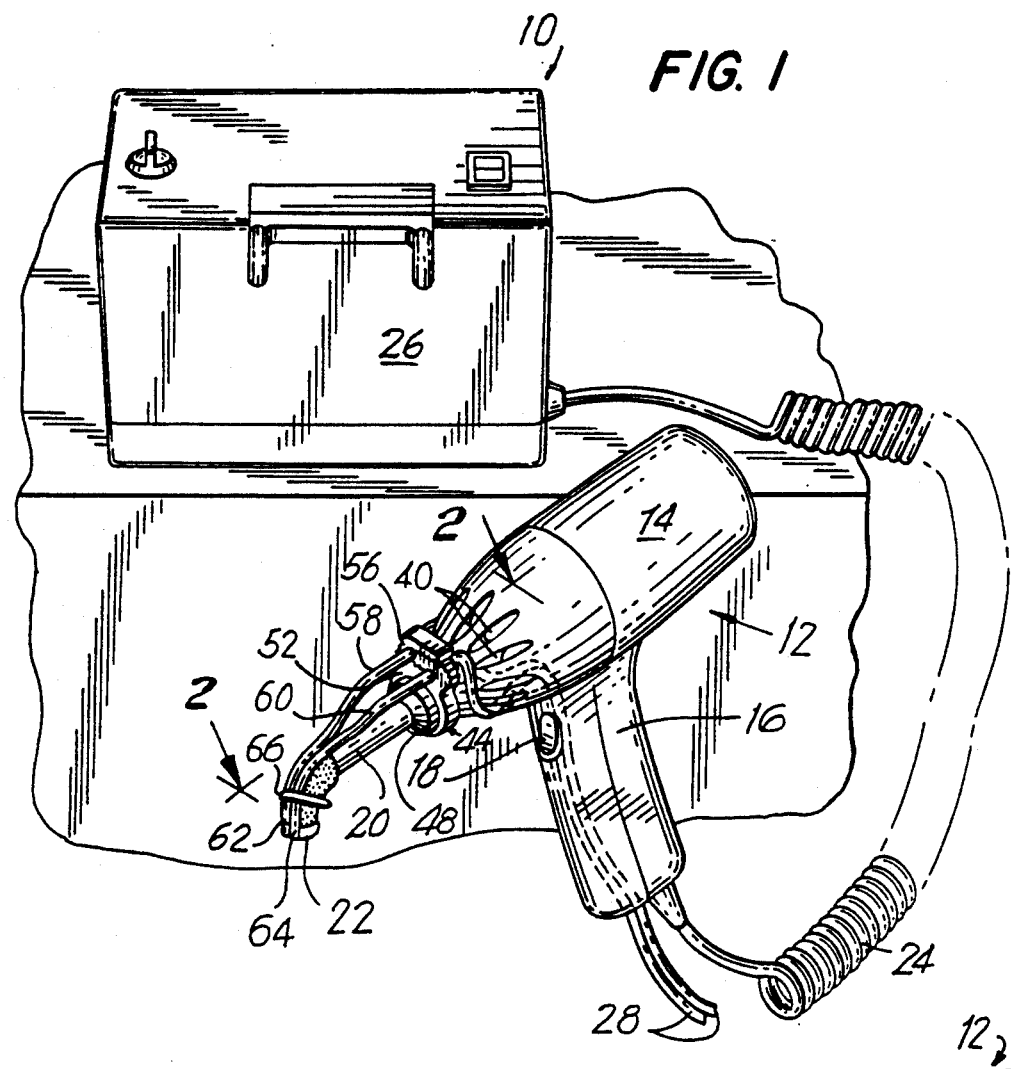
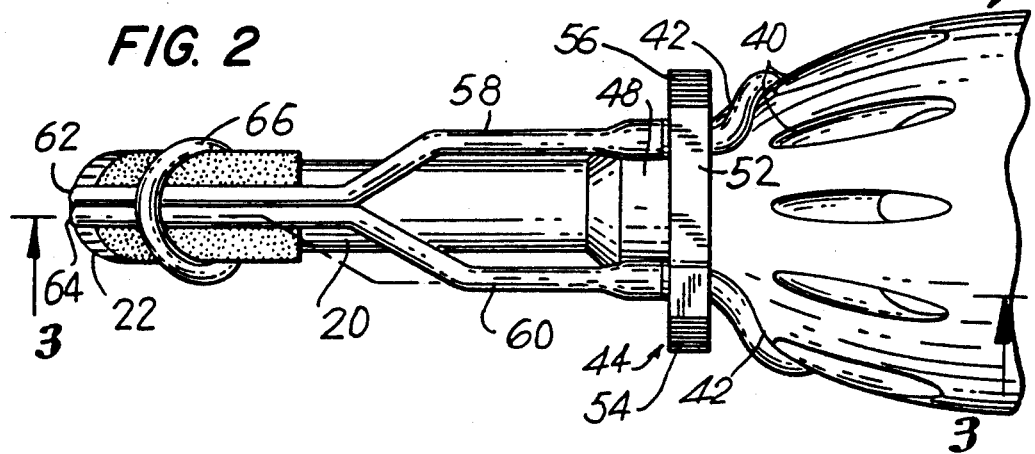

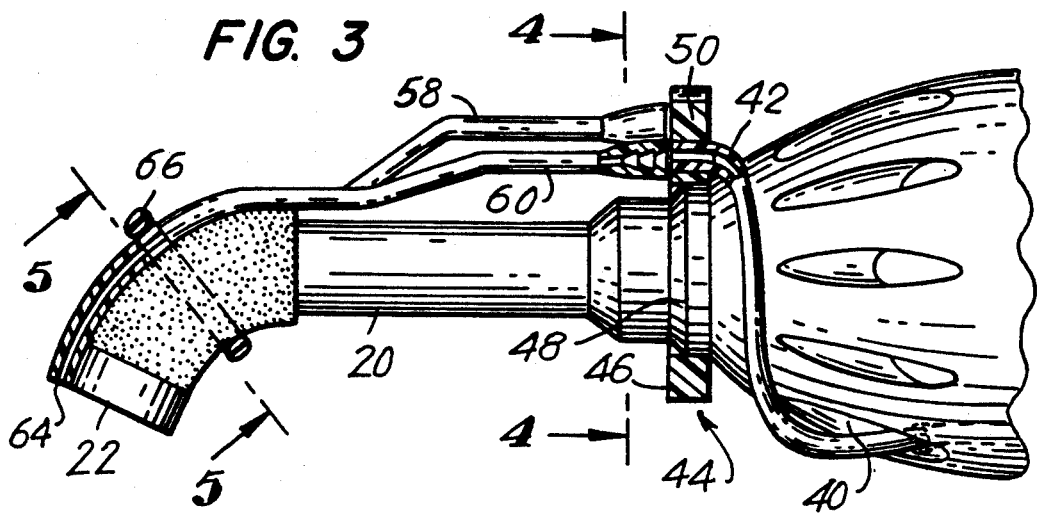
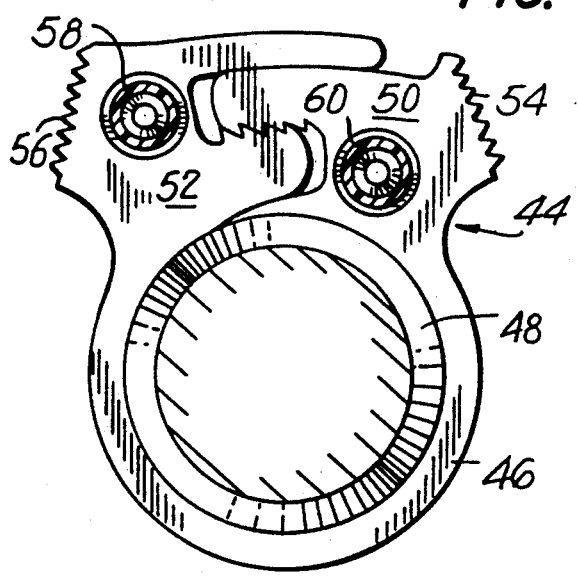
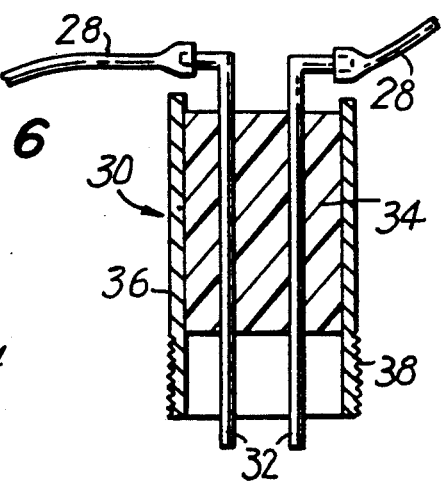

AIR/WATER DELIVERY SYSTEM FOR USE WITH DENTAL ILLUMINATION DEVICES

The present invention relates to the dental arts and, in particular, to an apparatus for the provision of compressed air and/or water to the site of a dental procedure in conjunction with the use of a dental illuminating, light curing device.

BACKGROUND OF THE INVENTION

The use of a dental apparatus for the illumination of an oral procedure site is well known. Typically, such illumination is often utilized as a source of activation energy for restorative compositions which are designed to set or cure upon the receipt of light of a certain bandwidth. Such compositions are used in a variety of procedures to rebuild tooth structures. The light is provided through a handpiece having a trigger to operate the light source on demand.

Various illumination devices have been provided within one or more supply lines having exit apertures in the handpiece for the simultaneous application of compressed air and/or water to the location. For example, U.S. Pat. No. 4,975,058 of Dec. 4, 1990 to Woodward discloses a dental handpiece having lines providing for a handpiece drive air, exhaust air, chip removal air, water and light. U.S. Pat. No. 4,826,431 of May 2, 1989 to Fujimura discloses a dental handpiece utilizing a laser light source intended, among other objectives, to provide hardening of optically polymerized substances. The handpiece is further adapted to transmit water and air as may be desired. Such handpieces typically utilize a variety of switches and controls on the handpiece proper to allow the practitioner to apply the appropriate combination of light, water and air as may be appropriate for the procedure at hand. It is often difficult or inconvenient to manipulate the various functions allowable for the device.

Many practitioners, however, utilize light sources, which do not incorporate either water or air supply means, and the practitioner is required either to utilize an assistant to operate a second water and air applicator or, alternatively, alternate use of the light source and water/air supply means by putting one unit down and picking up the other. Either alternative is inconvenient and inefficient. Replacement of the handpiece, however, with a combination unit may not be a viable alternative, because of the cost factor involved, the unavailability of such a combination light source having the illumination characteristics required for the restoration materials utilized, or the practitioner's inability to provide the necessary compatible connections for the water and air lines of such a combination unit.

It is thus the purpose of the present invention to provide an apparatus which permits a dental light source not having air and/or water supply means to be adapted to additionally provide air and/or water in association with the light Yet another purpose of the present invention is to provide an apparatus which allows a light source to be modified to provide air and water in a manner which does not disturb the normal functioning of the light source.

Still another purpose of the present invention is to provide such an apparatus which is compatible with standard dental water and air supply sources, and thus allows control over the air and water to be maintained by use of a conventional foot control which may be operated by the practitioner in the conventional manner.

BRIEF DESCRIPTION OF THE INVENTION

In accordance with the above and other purposes and objects, the apparatus of the present invention comprises a pair of air and water supply lines having a first end adapted to interfit with the air and water fittings on the typical dental supply pedestal, which normally supplies air and water in a controlled manner by use of a foot operated switch means. The lines extend to the illumination apparatus handpiece, and are affixed to the base of the neck of the apparatus, where they terminate by means of a clamp. A second clamp embraces the neck of the apparatus proximate the distal end thereof and supports pair of nozzles which terminate proximate the illumination tip to allow the air and water supplied to be dispensed at the location at which the dental work is being performed.

The nozzle elements are interconnectable with the main supply lines at the first neck clamp to complete the supply circuit. The nozzle means are removable to allow sterilization and/or replacement as required. When interconnected with the air and water supply, foot control over the air and water in the manner known to the practitioner allows control to be maintained without encumbering the illumination device with additional switches and/or valves. The supply lines may lie solely upon the exterior of the illuminator or, alternatively, may be fed through the interior thereof.

BRIEF DESCRIPTION OF THE DRAWINGS

A fuller understanding of the present invention will be obtained upon consideration of the following detailed description of a preferred, but nonetheless illustrative embodiment thereof when reviewed in association with the annexed drawings wherein:

FIG. 1 is a perspective view of a typical dental illuminator bearing the air/water delivery system of the present invention;

FIG. 2 is a top plan view of the nozzle portion of the illuminator taken along line 2—2 of FIG. 1, depicting the connection of the present invention to the neck of the illuminator;

FIG. 3 is an elevation view taken along line 3—3 of FIG. 2 further depicting the mounting of the present invention upon the illuminator device;

FIG. 4 is an elevation view in section taken along line 4—4 detailing the means by which the air and water supply lines are clamped to the illuminator;

FIG. 5 is an elevation view taken along line 5—5 of FIG. 3 depicting the mounting of the nozzle portion to the illuminator; and FIG. 6 is an elevation view in section depicting the main connector for the supply lines.

DETAILED DESCRIPTION OF A PREFERRED EMBODIMENT

With reference to FIG. 1, a typical dental illuminator device 10 intended for optically curing dental restorative materials includes a generally pistol-shaped handpiece 12 having an appropriate illumination source (not shown) located in body 14 and having a depending hand grip portion 16 with operating switch or trigger 18. A neck assembly 20 projects from the forward end of the body, and may include appropriate waveguides and filters to direct a beam of light outwardly from tip 22 onto the material to be cured. Such a device is exemplified by the Optilux 400 unit of Demetron Research Corporation of Danbury, Conn. The handpiece 12 is connected by electrical supply cord 24 to power supply 26, which may include a master power switch and timer circuitry, as well as transformer means to provide a relatively low operating voltage to the handpiece. As provided, the illuminator has no provision for dispensation of either water or air at the tip.

The present invention comprises a pair of supply lines 28, joining the handpiece to a source of air and water. As shown in FIG. 6, the distal ends of the supply lines are connected to adaptor 30, comprising a pair of coupler tubes 32 mounted within an elongated block or gasket 34. The tubes 32 are dimensioned to be insertable within the ends of the lines 28, and provide a secure, leak-free friction fit therein. The block or gasket 34 is mounted within adapter body 36, which is cylindrical and is provided with a exterior threading at 38. The diameter of the body 36 and the threading 38 are chosen to mate with the standard water and air supply connection fitting in a dental pedestal unit. Such fitting is normally provided with an internally threaded collar which will mate with the threaded portion of the adaptor body end and secure the adaptor to the fitting. The coupler tubes are chosen to be of the proper diameter to mate with the air and water supply lines in the fitting and are positioned within the block 34 to be insertable therein. The block itself may be formed of any appropriate material, typically a rubber or plastic compound.

As detailed in FIGS. 2 and 3, the proximal ends of the air/water supply lines 28 may be fed through the interior of the handpiece 14, typically entering through the lower end of hand grip 16 and exiting through a pair of ventilation holes 40 proximate the neck assembly 20, if present. Alternatively, other pre-existing apertures in the handpiece body may be utilized or appropriate bores may be added.

Neck coupling tubes 42, which may be of a general "S" shape and of appropriate metal such as stainless steel, are supported by first neck clamp 44 positioned at the base of the neck. The neck coupling tubes connect to the proximal ends of the supply lines 28, and are dimensioned to be insertable into the ends of the supply tubes and are retained by friction therein.

As shown in FIG. 4, the clamp 44 includes a generally circular clamping portion 46 sized to embrace the proximal end 48 of the handpiece neck assembly. A pair of complimentary, serrated arms 50, 52 extend from opposite ends of the clamping portion 46, and allow the clamp to be tightened about the neck portion, the serrations retaining the clamp about the neck when finger pressure is applied to the opposed hand grips 54, 56. Each of the clamp arms 50, 52 is provided with a through-bore through which the neck coupling tubes 40, 42 extend and by which the tubes are supported in place. When in position upon the neck portion 48, the clamp 44 maintains the coupling tubes and accordingly the supply lines 28 in position upon the handpiece 12.

To provide the water and air at the nozzle tip 22, a pair of nozzle hose elements 58, 60 are utilized. These hose elements connect at their proximal ends to the forward ends of neck coupling tubes 40, 42, and terminate at distal exposed ends 62, 64 positioned proximate to tip 22. Mounting gasket 66 surrounds and embraces the forward end of the neck 20 proximate tip 22, and, as best seen in FIG. 5, also engages the nozzle tubes 58 and 60, maintaining them in position as required. The gasket may be chosen of any appropriate material, such as rubber or plastic.

Fully mounted on the handpiece 12, the present invention allows water and air to be provided at the illuminator tip despite the fact that the illumination system 10 was not originally provided with such capability. Because the nozzle tubes 58, 60 are separate from the main supply tubes 28, they may be removed and replaced as required without disassembly of the entire system. As the neck portions 20 of illuminator systems are often interchangeable, the modular construction of the present invention allows appropriate nozzle tubes to be chosen, consistent with the length and shape of the neck portion with which it is to be used. Thus, air and water may be provided in conjunction with a variety of neck configurations without the necessity of complete interchange or modification of the supply system. In the event it is inconvenient or inappropriate to position the supply lines 28, 28, through the handpiece body, they may alternatively be located solely on the exterior of the unit. In such a case an appropriate clamp (not shown) may be utilized to further hold the supply tubes in fixed position along the handpiece surface.

Because the illuminator is not encumbered with additional switches, levers, valves, and the like, the practitioner can remain familiar with the control of the illuminator. Full control is maintained over the air and water supplies by the standard dental foot control which now becomes an integral part of the system. As the dentist is typically fully familiar and comfortable with operation of the foot control, the water and air supplies are conveniently and efficiently controlled.

It is to be recognized by those skilled in the art that the foregoing description is illustrative only, and that modification and adaptation of the present invention may be accomplished without departing from the spirit or scope thereof.

I claim:

1. An apparatus for the provision of air and water to the tip of a dental illuminator having a neck terminating at an illumination tip extending from a handpiece, said handpiece further comprising a hand-grip portion, said dental illuminator being operatively connected to an illumination power supply independent of a dental pedestal and without a water or air supply, said apparatus comprising a pair of supply lines having first and second ends, said first ends adapted to connect to air and water supplies on a dental pedestal; a first clamp adapted to be mounted to the neck of said illuminator proximate the handpiece; a pair of connector tubes each having a first end adapted to connect with a second end of one of said supply tubes and a second end adapted to be mounted on and supported by said first clamp, the terminating portions of said supply tubes proximate said second ends projecting through said clamp towards the tip of said illuminator; a second clamp adapted to be mounted to the dental illuminator neck proximate the illumination tip; and a pair of nozzle tubes each having a first end adapted to dispense the supplied material and positioned proximate the tip of the illuminator and being held in position with respect thereto by said second clamp, said second ends of said nozzle tubes being removably connected to said second ends of said connector tubes.

2. The apparatus of claim 1, wherein said first clamp comprises a clamp body having a pair of opposed serrated ends adapted to interengage and retain said body in engagement about said neck; said clamp body having a pair of apertures therethrough to support said connector tubes.

3. The apparatus of claim 2, wherein said second clamp is a gasket formed of an elastomeric material adapted to surround and embrace said nozzle tubes and said neck.

* * * * *